United States Patent [19]

Doane et al.

[11] Patent Number: 4,911,952

[45] Date of Patent: Mar. 27, 1990

[54] ENCAPSULATION BY ENTRAPMENT WITHIN MATRIX OF UNMODIFIED STARCH

[75] Inventors: William M. Doane, Morton, Ill.; Sukumar Maiti, Kharagpur, India; Robert E. Wing, Peoria, Ill.

[73] Assignee: The United States of America as represented by the Secretary of Agriculture, Washington, D.C.

[21] Appl. No.: 72,201

[22] Filed: Jul. 10, 1987

[51] Int. Cl.$^4$ .............................. B01J 13/02; A61J 3/07
[52] U.S. Cl. ................................ 427/213.31; 264/4.1; 424/410; 424/488; 428/402.24; 514/965; 71/64.11; 71/DIG. 1; 426/103
[58] Field of Search ............... 264/4.1; 424/410, 488; 514/965; 428/402.24; 71/DIG. 1, 64.11; 426/103; 427/213.31

[56] References Cited

U.S. PATENT DOCUMENTS

| | | | |
|---|---|---|---|
| 2,876,160 | 3/1959 | Schoch et al. | 167/82 |
| 3,159,585 | 12/1964 | Evans et al. | 426/103 X |
| 3,499,962 | 3/1970 | Wurzburg et al. | 424/35 |
| 3,666,557 | 5/1972 | Jensen et al. | 127/32 |
| 3,922,354 | 11/1975 | Galluzzi et al. | 426/96 |
| 4,230,687 | 10/1980 | Sair et al. | 424/22 |
| 4,277,364 | 7/1981 | Shasha et al. | 252/316 |
| 4,382,813 | 5/1983 | Shasha | 71/64.11 X |
| 4,755,397 | 7/1988 | Eden et al. | 426/103 X |
| 4,812,445 | 3/1989 | Eden et al. | 514/60 |

FOREIGN PATENT DOCUMENTS 04074 9/1985 Canada .

*Primary Examiner*—John F. Terapane
*Assistant Examiner*—Gary L. Geist
*Attorney, Agent, or Firm*—M. Howard Silverstein; Curtis P. Ribando; John D. Fado

[57] ABSTRACT

Chemical biological agents to be encapsulated are blended into an aqueous dispersion of an unmodified starch comprising about 5% to about 25% by weight amylose. The dispersion, having an initial starch solids content of about 20% by weight, is characterized by completely disrupted starch granules and completely disassociated amylose molecules that are not significantly depolymerized. Subsequent drying is accomplished by reassociation of the amylose molecules which converts the dispersion into a protective matrix and binds the agents within the interstices of the reassociating starch chains. Rate of release of agents to the environment can be altered by varying the proportion of amylose in the starch. Encapsulation of biologically active compositions provides protection against degradative environmental conditions, improves safety in handling, and slows the release of such compounds to the surrounding medium.

22 Claims, No Drawings

ENCAPSULATION BY ENTRAPMENT WITHIN MATRIX OF UNMODIFIED STARCH

BACKGROUND OF THE INVENTION

1. Field of the Invention

This invention relates to a simple, novel method of encapsulating agricultural chemicals, food constituents, medicaments, and other chemical biological agents for controlling their release, and to the compositions prepared thereby.

2. Description of the Prior Art

Various approaches to the controlled release of chemical biological agents by means of a starch-based encapsulating material have been disclosed previously. Some of these methods have involved the use of chemical crosslinking reactions. In U.S. Pat. No. 4,382,813, Shasha discloses a system for encapsulating certain types of pesticidal agents by the rapid insolubilization of a starch-containing material alkoxide with a bivalent cation selected from the group of calcium, barium, and strontium. While this system is applicable to water-insoluble agents, it is not particularly suitable for those which are water soluble, nor for substances susceptible to alkali degradation.

In U.S. Pat. No. 4,439,488, Trimnell et al. disclose a method of encapsulation wherein entrapment is achieved by insolubilization of a polyhydroxy polymer with boric acid or a boric acid derivative at a mildly alkaline pH. This system is applicable to a broader spectrum of active agents than that of Shasha, supra, but is not suitable for products intended for human ingestion.

Controlled release by means of starch-based encapsulating materials can also be accomplished without the use of chemical crosslinking reactions. In U.S. Pat. No. 2,876,160, Schoch et al. disclose such a method which employs modified, amylose-free starches at concentrations up to 65% solids for embedding water-insoluble materials.

In PCT Int. Appl. WO 85/04074, Flashinski et al. disclose two methods of preparing a starch gel matrix containing an insecticide. The insecticide is either coextruded with a dilute, aqueous dispersion of starch, or the starch is first partially cooked in an extruder prior to cold-blending with the insecticide. In either case, the product is recovered and used as an aqueous gel.

In U.S. Pat. No. 4,230,687, Sair et al. disclose the application of shearing stress, vigorous mechanical working, and heat to distribute active agent into an enveloping matrix of chemically modified starches, gums, and proteins in the presence of a limited quantity of water. Proteins are used for slow-release matrices; modified starches are used for rapid release.

Similarly, in U.S. Pat. No. 3,922,354, Galuzzi et al. disclose the use of high-shear mixing to incorporate active agents into low-water, high-solids matrices prepared from partially gelatinized unmodified starches. Additives such as modified dextrins, mixtures of mono- and diglycerides, toasted cereal solids, and coloring agents are used to control the release of active agents.

In U.S. Pat. No. 3,666,557, Jensen et al. disclose a method of using low-fat starchy materials to microencapsulate individual beadlets of sensitive materials such as vitamins and vegetable oils. Starches are prepared for encapsulation by heating at 88° C. for 30 min followed by passage through a homogenizer to effect disruption of granules without degradation of molecules.

SUMMARY OF THE INVENTION

We have now unexpectedly discovered a method of achieving substantially complete encapsulation of virtually all types of chemical biological agents in a starch system without the use of chemical crosslinking reagents. The agents are blended into an aqueous dispersion of amylose-containing, unmodified starch, in which reassociation of amylose molecules occurs when the mixture cools. This reassociation forms a continuous, insolubilized matrix entrapping discontinuous domains of the agent within the interstices of the reassociated chains.

In accordance with this discovery, it is an object of the invention to provide a facile, universal, and industrially acceptable method for encapsulation of core materials.

It is also an object of the invention that the primary matrix-forming material be derived from natural renewable resources.

Another object of the invention is that the primary matrix-forming material be safe for human ingestion.

It is a further object of the invention to provide a novel free-flowing particulate product in which discontinuous domains of biologically active core materials are entrapped by a continuous matrix of starchy material.

Another object of the invention is to provide a product in which the encapsulated substance is sufficiently protected to be safe for handling, controllably released to a wide variety of environments, and resistant to losses by volatilization, leaching, wind transport, air oxidation, digestion, and sunlight decomposition.

Other objects and advantages of this invention will become readily apparent from the ensuing description.

DETAILED DESCRIPTION OF THE INVENTION

The starting encapsulating material contemplated for use in the invention includes unmodified natural granular starches such as regular cereal, potato, and tapioca starch, and flours containing the same, as well as mixtures of these with waxy starches and high-amylose starches. Full-fat starches, that is, starches which have not had a portion of the bound fat removed, are suitable for use herein.

Starch is a low-cost and abundant natural polymer composed of amylose and amylopectin. Amylose is essentially a linear polymer having a molecular weight in the range of 100,000-500,000, whereas amylopectin is a highly branched polymer having a molecular weight of up to several million. When starch is gelatinized in water and cooled, the amylose retrogrades to a much greater extent than the amylopectin fraction. Retrogradation is a term applied to the phenomenon whereby starch chains in dispersion associate, become insoluble, and precipitate. The rate and extent of retrogradation depend on properties of dispersion (pH, temperature, concentration) and on the amount of amylose present in the dispersion. While common cornstarch (pearl) contains about 25% amylose and 75% amylopectin, the waxy corn starches contain only amylopectin and those referred to as high-amylose starches contain up to 75% amylose.

The starch is prepared for encapsulation by thorough dispersion in water under conditions that completely disrupt the starch granules and completely disassociate essentially all the amylose molecules without significant depolymerization. Such dispersion is accomplished with starches having amylose contents of up to about 25% when an aqueous slurry of the starch is passed through a steam-injection cooker at a temperature of about 120°–135° C. Starches having greater than about 25% amylose require temperatures of about 155°–160° C. Gelatinization at lower temperatures does not allow complete granule rupture, while gelatinization at higher temperatures causes some starch depolymerization. Steam-injection cooking is a preferred method of gelatinization because it affords the advantage of providing a continuous process and because disruption of starch granules is accomplished rapidly and completely in one step. Alternatively, extrusion cooking will effectively achieve the gelatinization. For purposes of this invention, the starch dispersion is considered to be in the aqueous phase, which will constitute the continuous phase of the encapsulation system. The specified starches prepared in this manner are effective to achieve encapsulation without the presence of any additional encapsulating agent.

Chemical biological agents which are suitable for use herein may be any organic or inorganic solids capable of being finely divided or any liquid, provided that the agent does not interfere with the encapsulating process, and does not react with or dissolve the encapsulating matrix. Particularly envisioned are chemicals and chemical formulations which meet the above criteria and which are classified as a known herbicide, insecticide, fungicide, nematocide, bactericide, rodenticide, molluscicide, acaricide, larvacide, fumigant, animal repellant, plant growth regulator, fertilizer, pheromone, flavor composition, odor composition, vitamin, mineral, or medicament.

Exemplary agents within the scope of the invention are categorized below:
  Herbicides:
S-ethyl dipropylthiocarbamate [EPTC, "Eptam"],
α,α,α-trifluoro-2,6-dinitro-N,N-dipropyl-p-toluidine [trifluralin, "Treflan"],
S-ethyl diisobutylthiocarbamate [butylate, "Sutan"],
2,6-dichlorobenzonitrile,
1,1'-dimethyl-4,4'-bipyridinium dichloride,
2,4-dichlorophenoxy acetic acid,
sodium 2,4-dichlorophenoxy acetate, and
ammonium 3-amino-2,5-dichlorobenzoate,
2-chloro-2',6'-diethyl-N-(methoxymethyl)acetanilide [alachlor, "Lasso"],
2-chloro-N-(2-ethyl-6-methylphenyl)-N-(2-methoxy-1-methylethyl)acetamide [metolachlor, "Dual"].
  Nematocide:
1,2-dibromo-3-chloropropane.
  Insecticides:
O-ethyl-S-phenylethyl phosphorodithioate,
S-(1,2-dicarbethoxyethyl)-O,O-dimethyl dithiophosphate,
methyl O,O-dimethyl-o,p-nitrophenyl phosphorothioate,
1,1,1-trichloro-2,2-bis(p-chlorophenyl), and
2,3-dihydro-2,2-dimethyl-7-benzofuranyl methyl carbamate.
  Sex lures or attractants:
methyl 4-allyl-2-methoxyphenol, and
tertiarybutyl 4-chloro-2-methyl cyclohexane carboxylate.
  Pesticides:

For comprehensive lists of pesticide compositions, see O. Johnson, Chemical Week, pp. 39–64 (June 21, 1972).
  Fungicide:
benomyl[methyl 1-(butyl carbamoyl)-2-benzimidazole carbamate]["Banlate"]
  Water soluble vitamin:
vitamin C (ascorbic acid)
  Fat soluble vitamins:
vitamin A (trans Retinol),
vitamin $D_2$ (ergocalciferol)
  Attractants:
4-allylguaiacol eugenic acid (eugenol),
1,2-dimethoxy-benzene ("Veratrole"),
1-methoxy-4-propenyl-benzene ("Anethole"),
1-benzo[b]pyrrole ("Indole"), and
α-tolualdehyde
  Essential oils:
orange oil (linonene),
cinnamon oil, and
citronella oil
  Flavorants:
almond,
menthol, and
vanillin
  Proteins, enzymes, and amino acids:
casein
protease,
lysine
  Nutrients:
urea,
sulfur
  Micronutrients:
boron (as borate),
copper (as copper sulfate),
cobalt (as cobalt sulfate),
iron (as ferrous sulfate),
manganese (as manganese sulfate),
molybdenum (ammonium molybdate), and
zinc (as zinc sulfate)
  Vegetable oil:
corn oil
  Antibiotic:
aureomycin (chlortetracycline hydrochloride).

Other compositions suitable as core materials for use in accordance with the invention will be known to those skilled in the art. Core materials dissolved, emulsified, or otherwise dispersed in solvents or carriers, as well as compatible combinations of the above types of compositions are also easily encapsulated by the instant method.

The core material to be encapsulated is blended with the starch dispersion by any conventional means of obtaining a relatively uniform distribution. The domains of the agent, which constitute the discontinuous phase of the mixture, should be sufficiently small to render the mixture stable until the amylose components reassociate with one another and entrap the core material. It would be within the skill of a person in the art to determine the maximum level at which a particular agent can be effectively loaded into the system. However, based on the use of butylate (Example 27), it is clear that as much as 18% active ingredient by weight can be incorporated into the dispersion with 88% encapsulation. For purposes of performance, effective amounts of core materials depend entirely on the type and characteristics of the core material, on matrix thickness, and on the intended utility of the product. A very volatile liquid, for instance, would require a thicker structure than a nonvolatile solid, and accordingly should be incorporated at a lower level. Similarly, a volatile liquid to be completely withheld from the environment would be incorporated at a lower level than one to be used as a slow-release pesticide. "An effective amount of a suitable chemical biological agent" is defined herein as that amount of core material which will achieve the desired result (e.g., attract, repel, or kill pests; release a detectable aroma, flavor, nutrient, or pharmaceutically active dosage of medicament; or enhance the growth of plants) when the encapsulated composition containing the effective amount of the agent is placed in the proper environment.

Encapsulation is accomplished without the use of any chemical additives or modifiers by the simple and convenient process of dehydrating or drying the starch-agent mixture under conditions that allow the amylose components of the starch to reassociate. The result is a substantially homogeneous mass analagous to the precursive mixture in which, now, discontinuous domains of active ingredient are uniformly dispersed throughout a continuous matrix. This process distinguishes from microencapsulation which yields discrete particles, each comprising a domain of agent enveloped by a film or coating of encapsulating agent.

The recovery procedure is aimed at converting the homogeneous mass to discrete, free-flowing, nonagglomerating particles. In accordance with one method of recovery contemplated herein, the starch-agent mixture is placed on trays and dried at 30° C. for 16 hr or at 130° C. for 90 min. The resulting film is readily ground into small, nonagglomerating particles. In an alternate embodiment, the starch-agent mixture is worked in a sigma-blade mixer under a stream of air until sufficient moisture is lost that crumbling occurs (see Examples 46–51, Table XI). The resulting particles may be easily washed, filtered, dried, and further ground if necessary by any conventional methods. In some cases further grinding is not necessary. Dewatering can also be conducted in an extruder, The level of encapsulation is affected by the concentration of amylose in the starch; as the amylose concentration increases above about 10%, the percent encapsulation of active agent decreases (Examples 1–7, Table I). This phenomenon is explained by the alignment of the linear amylose chains in the retrogradation process. The resulting hydrogen bonding exudes part of the active agent to the gel surface where it evaporates. However, the agent that becomes entrapped is released slower in the presence of more amylose because of the greater strength of polymer interaction. In contrast, when the amylose content is 5% or less, very little retrogradation occurs and the matrix will disperse almost completely in water. The influence of amylose concentration is similarly reflected in the amount of swelling of products when submerged in water. It is apparent, therefore, that release characteristics of the starch matrices are controlled simply and conveniently, without the use of chemical treatments or additional processing, by altering the proportion of amylose in the starch. The operable proportion is considered to be within the range of about 2-75% amylose by weight of the starch, with the preferred range being about 10-25%. This preferred range of amylose concentrations is easily obtained by using different combinations of pearl cornstarch with waxy starch.

The following examples are intended only to further illustrate the invention and are not intended to limit the scope of the invention which is defined by the claims.

EXAMPLES 1–7

A graded series of mixtures of unmodified granular cornstarches, which contained varying proportions of waxy (0% amylose) and pearl cornstarch (25% amylose) calculated to provide amylose in the amounts listed in Table I, was used for encapsulation (Examples 1–5), along with two samples of high-amylose starch (Examples 6 and 7). The general procedure was as follows: 90 g of starch was slurried in 180 ml of water (33% solids) and passed through a continuous steam-injection cooker at 135° C. The amount of steam allowed to enter the cooker was used to regulate the gelatinization temperature, and the back pressure was kept constant. During gelatinization, pastes became diluted by as much as 100% because of steam condensation. The gelatinized starch paste was collected in a Dewar flask from the cooker and transferred to a sigma-blade mixer. Ten grams of butylate [S-ethyl bis(2-methyl propyl)carbamomethioate] was added with mixing, and mixing was continued for 30 min at 81 rpm. The mixture was transferred to trays and dried at 30° C. for 16 hr. The resulting film was ground in a Waring blender to a free-flowing powder.

The amount of butylate in the ground products was determined by gas-liquid chromatography (GLC) and was reported as butylate encapsulated, expressed as percent of the amount initially added. The ground products were washed with hexane, treated with 2N HCl at 100° C. for 5 min, and extracted with isooctane. After the resulting products were shaken with excess water for 4 hr, the amount of butylate in the water was compared with that in the products before shaking and reported as percent butylate released. The results of these determinations are given in Table I. Also included in the table are measurements of the increase in volume of pulverized products (0.2 g) after submersion in water (4 ml) for 24 hr (matrix volume increase, expressed as percent of initial solid volume).

The data in Table I demonstrate that effective encapsulation and a wide range of release rates can be achieved with the use of amylose contents from about 5% to about 70% of the starch weight.

TABLE I

| Example | % Amylose | % Butylate encapsulated | % Butylate released | % Matrix volume increase |
|---|---|---|---|---|
| 1 | 5 | 94 | 100 | dispersed |
| 2 | 10 | 100 | 85 | almost dispersed |
| 3 | 15 | 93 | 54 | 380 |
| 4 | 20 | 89 | 46 | 320 |
| 5 | 25 | 89 | 43 | 280 |
| 6 | 50[a] | 74 | 30 | 190 |
| 7 | 70[b] | 51 | 24 | 180 |

[a]"Amylon V" starch.
[b]"Amylon VII" starch.

EXAMPLES 8–15

Ninety-gram portions of granular pearl cornstarch each were slurried in a sufficient amount of water to give the starch concentrations listed in Table II and passed through a steam-injection cooker as described in Examples 1–7. All the remaining procedures of Examples 1–7 for the encapsulation of butylate were repeated. The results of the analytical determinations (Table II) show that starch concentrations less than 20% are noticeably less effective for encapsulation and are, therefore, outside the scope of this invention. Jet cooking at higher solids loading is advantageous economically because less water has to be removed to recover dry product. Higher starch concentrations also give final products that swell less in water because retrogradation is enhanced by the lower amount of water available in the cooked starch dispersion and, therefore, less interference with the alignment of starch molecules.

EXAMPLES 16–20

Ninety-gram portions of granular pearl cornstarch each were slurried in 360 ml of water and passed through a steam-injection cooker at the temperatures listed in Table III. All the remaining procedures of Examples 1–7 for the encapsulation of butylate were repeated. Table III shows that temperatures between 120°–135° C. allowed the optimum recovery of active agent. Cooking at lower temperatures does not effect complete rupture of granules, while treatment at higher temperatures probably causes some starch depolymerization.

TABLE II

| Example | % Starch | % Butylate encapsulated | % Butylate released | % Matrix volume increase |
|---|---|---|---|---|
| 8 | 5 | 82 | 63 | 680 |
| 9 | 10 | 84 | 52 | 520 |
| 10 | 15 | 84 | 47 | 400 |
| 11 | 20 | 96 | 38 | 340 |
| 12 | 25 | 100 | 40 | 300 |
| 13 | 30 | 100 | 38 | 280 |
| 14 | 33 | 98 | 31 | 240 |
| 15 | 35 | 96 | 33 | 240 |

TABLE III

| Example | Cooking temperature (°C.) | % Butylate encapsulated | % Butylate released | % Matrix volume increase |
|---|---|---|---|---|
| 16 | 93 | 87 | 45 | 340 |
| 17 | 107 | 81 | 63 | 320 |
| 18 | 121 | 100 | 45 | 320 |
| 19 | 135 | 100 | 56 | 380 |
| 20 | 143 | 70 | 66 | 500 |

EXAMPLES 21–22

Ninety-gram portions of granular pearl cornstarch each were slurried in 360 ml of water and treated according to the procedure described in Examples 1–7 except that one of the starch-butylate mixtures was dried at 30° C. for 16 hr and the other was dried at 130° C. for 90 min. The results of the analytical determinations are given in Table IV.

EXAMPLES 23–27

Ninety-gram portions of granular pearl cornstarch each were treated according to the procedures described in Examples 1–7 except that butylate was added in the varying amounts listed in Table V, which also shows the characteristics of the products.

EXAMPLE 28

A 90-g sample of corn flour (about 20% amylose) was used in accordance with the general procedure of Examples 1–7. The value for butylate encapsulated was 84%; for butylate released, 37%; and for volume increase, 240%. These values are all slightly lower than those for pearl corn starch (Example 5).

EXAMPLE 29

A 90-g sample of potato starch (about 25% amylose) was used in accordance with the general procedure of Examples 1–7. The value for butylate encapsulated was 90%; for butylate released, 56%; and for volume increase, 280%.

EXAMPLE 30

A 90-g sample of unmodified wheat starch (about 25% amylose) was used in accordance with the general procedure of Examples 1–7. The value for butylate encapsulated was 95%; for butylate released, 85%; and for volume increase, 320%.

TABLE IV

| Example | Drying temperature (°C.) | % Butylate encapsulated | % Butylate released | % Matrix volume increase |
|---|---|---|---|---|
| 21 | 30 | 89 | 32 | 260 |
| 22 | 130 | 96 | 38 | 340 |

TABLE V

| Example | Butylate (g) | % Butylate encapsulated | % Butylate released | % Matrix volume increase |
|---|---|---|---|---|
| 23 | 8 | 98 | 50 | 240 |
| 24 | 10 | 85 | 43 | 280 |
| 25 | 12 | 88 | 35 | 240 |
| 26 | 16 | 88 | 29 | 260 |
| 27 | 20 | 88 | 18 | 240 |

EXAMPLES 31–32

A 90-g sample of "Amylon VII" was used in accordance with the general procedure of Examples 1–7 except a 155° C. cooking temperature was used. Part of the sample was also oven dried at 130° C. for 90 min. The results of analytical determinations are given in Table VI.

EXAMPLE 33

A 90-g sample of "Amylon VII" was used in accordance with the general procedure of Examples 1–7 using "Eptam 7E" as the active agent. The value for "Eptam 7E" encapsulated was 68%; for "Eptam 7E" released, 64%; and for volume increase, 180%. The values are all slightly lower than those for pearl cornstarch (Example 62).

EXAMPLE 34

A 90-g sample of potato amylose was used in accordance with the general procedure of Examples 1–7 except the cooking temperature was 157° C. The value for butylate encapsulated was 47%; for butylate released, 63%; and for volume increase, 240%.

EXAMPLE 35

A 90-g sample of potato amylose (2 g.) and waxy starch (88 g.) was used in accordance with the general procedure of Examples 1–7. The amylose content was 2.4%. The value for butylate encapsulated was 98%; for butylate released, 100%; and for volume increase, dispersed.

EXAMPLES 36-37

Ninety-gram portions of cornstarch (18 g pearl and 72 g waxy) representing an amylose content of 5%, each were slurried in a sufficient amount of water to give the starch concentrations listed in Table VII and passed through a steam-injection cooker as described in Examples 1-7. All the remaining procedures of Examples 1-7 for the encapsulation of butylate were repeated. The analytical results are given in Table VII.

TABLE VI

| Example | Drying condition | % Butylate encapsulated | % Butylate released | % Matrix volume increase |
|---|---|---|---|---|
| 31 | air | 66 | 43 | 200 |
| 32 | oven | 57 | 55 | 160 |

TABLE VII

| Example | % Starch | % Butylate encapsulated | % Butylate released | % Matrix volume increase |
|---|---|---|---|---|
| 1 | 33 | 94 | 100 | dispersed |
| 36 | 40 | 88 | 100 | dispersed |
| 37 | 45 | 99 | 100 | dispersed |

EXAMPLES 38-40

Ninety-gram portions of granular pearl cornstarch each were used in accordance with the general procedure of Examples 1-7 except the addition of butylate was made at different starch paste temperatures in the sigma mixer. The temperatures and analytical results are given in Table VIII.

EXAMPLES 41-43

Ninety-gram portions of pearl cornstarch were used in accordance with the general procedure of Examples 1-7 except the pH of the starch slurry was adjusted with hydrochloric acid or 5N NaOH before cooking. The analytical results are given in Table IX.

EXAMPLES 44-45

Portions (454 g) of granular pearl cornstarch each were slurried in water (908 ml) and passed through a steam-injection cooker at 135° C. The gelatinized starch was transferred to a small sigma-blade mixer. Active agents (Table X) were each added and mixing was continued until the mass dehydrated to form a crumb. The results of the analytical determinations of the 20-40 mesh fraction are given in Table X.

EXAMPLES 46-51

Portions (2724 g) of granular pearl cornstarch each were slurried in water (5448 g) and passed through a steam-injection cooker at 135° C. The gelatinized starch paste was transferred to a large sigma-blade mixer. Corn oil (120 g) containing an indicator (p-amino azobenzene, 182 mg) was added with mixing.

The mixture was steam-heated for 0-2.5 hr to increase the rate of water removal. The time was recorded when the product became a crumb, and its moisture content was determined. Mixing was continued until the final product was 10% moisture. The indicator concentration was determined by UV as a measure of surface and encapsulated corn oil. Results are reported in Table XI.

TABLE VIII

| Example | Temperature of starch paste (°C.) | % Butylate encapsulated | % Butylate released | % Matrix volume increase |
|---|---|---|---|---|
| 38 | 90 | 96 | 34 | 220 |
| 39 | 60 | 98 | 31 | 240 |
| 40 | 30 | 94 | 32 | 240 |

TABLE IX

| Example | pH | % Butylate encapsulated | % Butylate released | % Matrix volume increase |
|---|---|---|---|---|
| 41 | 3.0 | 97 | 60 | 260 |
| 42 | 6.0 | 89 | 43 | 280 |
| 43 | 10.0 | 91 | 46 | 280 |

TABLE X

| Example | Active agent | Weight added (g) | % Active agent recovered | % Matrix volume increase |
|---|---|---|---|---|
| 44 | corn oil | 20 | 100 | 220 |
| 45 | butylate | 20 | 86 | 280 |

TABLE XI

| Example | Heating time, hr | Paste temp. after heating, °C. | % Solids To sigma | % Solids After heating | At crumb | Crumb time, hr | Corn oil, % Surface | Corn oil, % Encapsulated |
|---|---|---|---|---|---|---|---|---|
| 46 | 0 | 73 | 28 | 28 | 65 | 17 | 9 | 84 |
| 47 | 0.5 | 66 | 26 | 32 | 65 | 13 | 7 | 89 |
| 48 | 1.0 | 52 | 27 | 35 | 64 | 10 | 14 | 68 |
| 49 | 1.5 | 43 | 26 | 45 | 63 | 6 | 12 | 77 |
| 50 | 2.0 | 40 | 27 | 50 | 56 | 4.5 | 18 | 82 |
| 51 | 2.5 | 40 | 27 | 54 | 58 | 3 | 12 | 84 |

EXAMPLES 52-57

Portions (2724 g) of granular pearl cornstarch each were slurried in water (5448 g) and passed through a steam-injection cooker at 135° C. The gelatinized starch was transferred to a sigma-blade mixer. Several active agents (Table XII) were each added and mixing was continued until the mass dehydrated to form a crumb. The results of the analytical determinations of the 20- to 40-mesh fractions are given in Table XII.

EXAMPLE 58

A 5.45-kg sample of pearl cornstarch was slurried in water (18.16 kg) was fed into a Readco twin screw extruder at a rate of 210 ml/min. The screw temperature was 131° C. The gelatinized starch paste (10 kg, 28% H$_2$O) was transferred to a sigma-blade mixer. Corn oil containing indicator was added with mixing. Mixing was continued until the crumb that formed had a moisture content of 10%. The value for corn oil encapsulated was 81%.

EXAMPLES 59-60

A 90-g sample of granular pearl cornstarch was used in accordance with the general procedure of Examples 1-7. After analysis (Example 59), a portion of the sample was stored in a forced air oven at 130° C. for 72 hr and then reanalyzed (Example 60). The results of analytical determinations are given in Table XIII.

TABLE XII

| Example | Active agent | Weight added (g) | % Active agent recovered |
|---|---|---|---|
| 52 | "Treflan EC" | 661 | 96 |
| 53 | corn oil | 305 | 100 |
| 54 | urea | 305 | 100 |
| 55 | lysine | 305 | 100 |
| 56 | "Lasso" | 678 | 94 |
| 57 | "Eradicane" | 347 | 88 |

TABLE XIII

| Example | % Butylate encapsulated | % Butylate released | % Matrix volume increase |
|---|---|---|---|
| 59 | 84.7 | 76 | 260 |
| 60 | 84.9 | 53 | 240 |

EXAMPLES 61-67

Ninety-gram portions of granular pearl cornstarch each were used in accordance with the general procedure of Examples 1-7 except several herbicides were encapsulated. The results of analytical determinations are given in Table XIV.

EXAMPLE 68

Bioassay Study

"Treflan EC" and the starch-encapsulated sample of "Treflan EC" (Example 65) were evaluated against a control by incorporation and surface application at the rate of 1 kg/ha to 10-cm² plastic Petri dishes containing 150 g soil at 16% moisture by weight. The tests were run at 0, 7, 14 days after the herbicide was applied against sorghum seeds. The number and weight of plant growth were determined and are reported in Table XV.

EXAMPLE 69

Glass columns (2 cm) were filled with acid-washed sand (50 g) which resulted in a 12-cm bed. The columns were loaded with "Eptam 7E" (12 mg), "Lasso 4E" (22 mg), the product of Example 62 (147 mg), the product of Example 33 (227 mg), or the product of Example 64 (137 mg). Distilled water was used for leaching and was delivered dropwise to the column from a 1000-ml separatory funnel. The effluent was collected at a rate of 2 ml/min and each fraction consisted of 10-ml volume. The mg of active agent in each fraction was determined by GC analysis, and the analytical results of this leaching study are shown in Table XVI.

EXAMPLE 70

The product of Example 61 was reanalyzed 7 months after preparation to determine if "Eptam" was lost or if the product retrograded further. The results of analytical determinations are given in Table XVII.

TABLE XIV

| Example | Active agent (g) | % Active agent encapsulated | % Active agent released | % Matrix volume increase |
|---|---|---|---|---|
| 61 | "Eptam 7E,"[a], 14 | 100 | 74 | 220 |
| 62 | "Eptam 7E", 8 | 72 | 72 | 200 |
| 63 | "Eptam 7E", 10 | 100 | 73 | 280 |
| 64 | "Lasso EC"[b], 22 | 92 | 27 | 240 |
| 65 | "Treflan EC"[c], 22.5 | 100 | 1 | 280 |
| 66 | "Sutan 6.7E"[d], 12 | 85 | 77 | 260 |
| 67 | "Dual"[e], 12 | 97 | 5 | 260 |

[a] Stauffer Chemical Co.; 88% a.i.
[b] Monsanto Chemical Co.; 45% a.i.
[c] Elanco Products Co.; 44% a.i.
[d] Stauffer Chemical Co.; 84% a.i.
[e] Ciba-Geigy; 84.4% a.i.

TABLE XV

| | Incorporated | | Surface applied | |
|---|---|---|---|---|
| Samples | Av. no. of plants | Av. wt. per plant (g) | Av. no. of plants | Av. wt. per plant, (g) |
| 0 Days | | | | |
| "EC" | 0 | 0 | 0 | 0 |
| Encapsulated product of Example 65 | 21.7 | 0.22 | 5.3 | 0.23 |
| Control | 19.3 | 0.28 | 23 | 0.22 |
| 7 Days | | | | |
| "EC" | 1 | 0.01 | 10.3 | 0.03 |
| Encapsulated product of Example 65 | 6.7 | 0.02 | 5.3 | 0.03 |
| Control | 11.7 | 0.30 | 5.7 | 0.30 |
| 14 Days | | | | |
| "EC" | 1.7 | 0.02 | 9 | 0.03 |
| Encapsulated product of Example 65 | 0.7 | 0.01 | 8 | 0.03 |
| Control | 27.7 | 0.14 | 15.3 | 0.23 |

TABLE XVI

| Total volume collected, (ml) | Total "Eptam 7E" eluted (mg) | Encapsulated product of Example 62 eluted (mg) | Encapsulated product of Example 33 eluted (mg) | Total "Lasso 4E" eluted (mg) | Encapsulated product of Example 64 eluted (mg) |
|---|---|---|---|---|---|
| 20 | 2.80 | 0.31 | 0.15 | 1.91 | 0.33 |
| 40 | 7.77 | 1.10 | 0.55 | 5.81 | 1.16 |
| 60 | 8.50 | 1.88 | 0.88 | 7.93 | 1.58 |
| 80 | 8.67 | 2.54 | 1.18 | 8.81 | 2.45 |
| 100 | 8.74 | 3.16 | 1.43 | 9.22 | 2.99 |
| 120 | 8.79 | 3.68 | 1.68 | 9.50 | 3.47 |
| 140 | 8.82 | 4.18 | 1.91 | 9.66 | 4.15 |
| 160 | 8.85 | 4.70 | 2.13 | 9.78 | 4.52 |
| 180 | 8.87 | 5.17 | 2.34 | 9.87 | 4.83 |
| 200 | 8.89 | 5.63 | 2.53 | 9.93 | 5.16 |
| 500 | 9.11 | 8.61 | 4.36 | 10.01 | 8.33 |

Ninety-gram portions of cornstarch (18 g pearl and 72 g waxy) representing an amylose content of 5%, each were used in accordance with the general procedure of Examples 1-7 except other active agents were encapsulated. The results as determined by GC or nitrogen analysis are given in Table XVIII.

EXAMPLES 76–79

Ninety-gram portions of granular pearl cornstarch each were used in accordance with the general procedure of Examples 1–7 except highly water-soluble active agents including nutrients, micronutrients, algicides, and sweeteners were encapsulated. The results as determined by atomic absorption or UV spectroscopy are given in Table XIX.

TABLE XVII

| Example | % "Eptam" encapsulated | % "Eptam" released | % Matrix volume increase |
|---|---|---|---|
| 61 | 100 | 74 | 220 |
| 70 | 100 | 78 | 210 |

TABLE XVIII

| Example | Active agent | % Active agent encapsulated | % Active agent released | % Matrix volume increase |
|---|---|---|---|---|
| 71 | limonene[a] | 73 | 100 | dispersed |
| 72 | casein[b] | 100 | 100 | dispersed |
| 73 | "Ultrazyme 93"[c] | 100 | 100 | dispersed |
| 74 | trans Retinol[a] | 100 | 100 | dispersed |
| 75 | ergocalciferol | 100 | 100 | dispersed |

[a]Aldrich Chemical.
[b]Sigma Chemical.
[c]Osmonics, Inc.

TABLE XIX

| Example | Active agent (g) | % Active agent encapsulated | % Active agent released | % Matrix volume increase |
|---|---|---|---|---|
| 76 | CuSO$_4$.5H$_2$O, 19.65 | 100 | 100 | 200 |
| 77 | urea, 10 | 100 | 100 | 380 |
| 78 | KMnO$_4$, 19.86 | 100 | 100 | 260 |
| 79 | aspartame, 1.0 | 100 | 100 | 240 |

EXAMPLE 80

Granular pearl cornstarch (90 g) and urea (10 g) in water (180 ml) was passed through a steam-injection cooker. The paste was transferred to a sigma-blade mixer and mixed for 30 min before air drying. The results of analytical determinations are compared to Example 77 in Table XX.

EXAMPLE 81

A 90-g sample of cornstarch (18 g pearl and 72 g waxy) representing an amylose content of 5%, was used in accordance with the general procedure of Examples 1–7 except the attractant eugenol (0.75 g) was encapsulated. The value for eugenol encapsulated was 100%; for eugenol released, 86%; and for volume increase, dispersed.

EXAMPLE 82

A 90-g sample of cornstarch (18 g pearl and 72 g waxy) representing an amylose content of 5%, was used in accordance with the general procedure of Examples 1–7 except the insecticide "Sevin" (0.1 g) and the attractant eugenol (0.01 g) were encapsulated at 100% efficiency.

EXAMPLE 83

A 90-g sample of granular pearl cornstarch was slurried in 360 ml of water and treated according to the procedure described in Examples 1–7 except that "Eptam 7E" (S-ethyl dipropylthiocarbamate) was substituted for butylate. Encapsulation was 100%; release, 72%; and volume increase, 280%. Since "Eptam 7E" is more soluble in water, the percent release was much higher than that of butylate.

EXAMPLE 84

Bioassay Study

The emulsifiable concentrate of EPTC ("Eptam 7E") and starch encapsulated sample of "Eptam 7E" as prepared above in Example 83 were surface applied at the rate of 6.72 kg/ha to 10 cm$^2$ plastic Petri dishes containing 150 g soil at 16% moisture by weight. The soil was kept at constant moisture using filter paper under the soil extended into a beaker of water. The Petri dishes were allowed to remain uncovered for 0 to 288 hr before they were bioassayed using pregerminated oat seeds (24 hr at 100% humidity). The experiment was conducted in the laboratory at 22° C. and was replicated four times. Shoot growth was measured 72 hr after bioassay was initiated, and data were compared to a standard curve to determine the kg/ha of EPTC remaining. The results are reported in Table XXI.

TABLE XX

| Example | % Urea encapsulated | % Urea released | % Matrix volume increase |
|---|---|---|---|
| 80 | 100 | 82 | 310 |
| 77 | 100 | 100 | 380 |

EXAMPLE 85

A 90-g sample of cornstarch was used in accordance with the general procedure of Examples 1–7 except the fungicide "Benlate" (2 g) was encapsulated. The value for "Benlate" encapsulated was 100%; for "Benlate" released, 15%; and for volume increase, 280%.

EXAMPLE 86

A 90-g sample of cornstarch was used in accordance with the general procedure of Examples 1–7 except the herbicide "Lasso" (22 g) and the fungicide "Benlate" (2 g) were encapsulated. The value for "Lasso" encapsulated was 96%; for "Lasso" released, 31%; and for volume increase, 240%.

EXAMPLE 87

A 90-g sample of cornstarch was used in accordance with the general procedure of Examples 1–7 except the herbicide "Eptam 7E" (11 g) and the fungicide "Benlate" (2 g) were encapsulated. The value for "Eptam" encapsulated was 84%; for "Eptam" released, 71%; and for volume increase, 260%.

EXAMPLE 88

A 90-g sample of pearl cornstarch was used in accordance with the general procedure of Examples 1–7 except aureomycin (chlortetracycline, 3 g) was encapsulated. The value for aureomycin encapsulated was 100%; for aureomycin released, 56%; and for volume increase, 320%.

TABLE XXI

| | % EPTC Remaining | |
| --- | --- | --- |
| Hours | EC | Encapsulated product of Example 83 |
| 0 | 100 | 100 |
| 24 | 59 | 98 |
| 48 | 23 | 98 |
| 96 | 44 | 74 |
| 144 | 9 | 84 |
| 192 | 4 | 53 |
| 288 | 0 | 5 |

EXAMPLE 89

A 454-g sample of granular pearl cornstarch was used in accordance with the general procedure of Examples 1–7 except corn oil (22 g) was encapsulated. The paste was mixed until it became a crumb of 20–40 mesh. The results of analytical determinations are given in Table XXII.

EXAMPLE 90

A 90-g sample of pearl cornstarch was cooked as described in Example 89 and mixed in a sigma blade mixer with a 200-g portion of the product of Example 89. Mixing was continued until the product became a 20- to 40-mesh crumb. The results of analytical determinations are given in Table XXII.

It is understood that the foregoing detailed description is given merely by way of illustration and that modification and variations may be made therein without departing from the spirit and scope of the invention.

TABLE XXII

| Example | % Corn oil encapsulated | % Corn oil on surface |
| --- | --- | --- |
| 89 | 66 | 34 |
| 90 | 83 | 17 |

We claim:

1. A method for the encapsulation of a biologically active chemical agent comprising the steps:
   a. providing at elevated temperatures a dispersion consisting essentially of an unmodified, amylose-containing starch and water having an initial solids content of at least about 20% by weight, wherein the amylose comprises from about 5% to about 25% of said starch on a dry weight basis, and wherein the granules of starch are completely disrupted and the amylose molecules of the starch are substantially completely disassociated from one another without significant depolymerization;
   b. blending said agent into said dispersion to form a mixture of the starch dispersion and the agent, wherein the relative amount of said solids with respect to the agent is sufficient to entrap the agent within a matrix of the starch; and
   c. treating the mixture consisting essentially of said starch, water and agent under dehydrating conditions at a temperature within the range of about 30°–130° C. whereby the amylose components will reassociate with one another and thereby transform said mixture into a continuous insolubilized matrix having entrapped therein uniformly dispersed, discontinuous domains of the agent.

2. The method of claim 1 wherein said starch is selected from the group consisting of pearl corn starch, corn flour, wheat starch, wheat flour, potato starch, potato flour, mixtures thereof, and mixtures thereof with waxy starch, high amylose starch, or the amylose fraction of a starch.

3. The method of claim 1 wherein the initial solids content of the dispersion is in the range of about 20–40% by weight.

4. The method of claim 1 wherein said starch dispersion is prepared by steam jet cooking.

5. The method of claim 1 wherein the elevated temperature is in the range of about 120°–135° C.

6. The method of claim 1 and further comprising the step of drying the mixture into a friable mass.

7. The method of claim 1 and further comprising the steps of drying the mixture into a friable mass, particularizing the friable mass into discrete particles, and recovering said particles.

8. The method as described in claim 1 wherein the biologically active chemical agent is a herbicide, insecticide, fungicide, nematocide, bactericide, rodenticide, molluscicide, acaricide, larvacide, fumigant, animal repellant, plant growth regulator, fertilizer, pheromone, flavor composition, odor composition, vitamin, mineral, or medicament.

9. A method for the encapsulation of a biologically active chemical agent comprising the steps:
   a. providing at elevated temperatures a dispersion consisting essentially of an unmodified, amylose-containing starch and water having an initial solids content of at least about 20% by weight, wherein the amylose comprises from about 5% to about 25% of said starch on a dry weight basis, and wherein the granules of starch are completely disrupted and the amylose molecules of the starch are substantially completely disassociated from one another without significant depolymerization;
   b. blending said agent into said dispersion to form a mixture of the starch dispersion and the agent, wherein the relative amount of said solids with respect to the agent is sufficient to entrap the agent within a matrix of the starch; and
   c. treating the mixture consisting essentially of said starch, water and agent under dehydrating conditions whereby the amylose components will reassociate with one another and thereby transform said mixture at a solids content in the range of about 55–65% into a continuous insolubilized matrix having entrapped therein uniformly dispersed, discontinuous domains of the agent.

10. A method as described in claim 9 wherein the initial solids content of the dispersion is in the range of about 20–40% by weight and said elevated temperature is in the range of about 120°–135° C.

11. A method for tailoring the release rate of a biologically active chemical agent encapsulated within a starch matrix, the method comprising:
   a. selecting an unmodified starch or mixture of unmodified starches having a ratio of amylose to amylopectin corresponding to a predetermined ratio of amylose and amylopectin needed to impart the desired release properties to said matrix wherein the amylose comprises from about 5% to about 25% of said starch or mixture of starches on a dry weight basis;
   b. dispersing said starch or mixture of starches at elevated temperatures in water at an initial solids content of at least about 20% by weight, wherein the granules of starch are completely disrupted and the amylose molecules of the starch are substantially completely disassociated from one another without significant depolymerization;

c. blending said agent into said dispersion to form a mixture of the starch dispersion and the agent, wherein the relative amount of said solids with respect to the agent is sufficient to entrap the agent within a matrix of the starch; and d. dehydrating the mixture consisting essentially of said starch, water and agent under conditions at a temperature within the range of about 30°–130° C. whereby the amylose components will reassociate with one another and thereby transform said mixture into a continuous insolubilized matrix having entrapped therein uniformly dispersed, discontinuous domains of the agent.

12. The method of claim 11 wherein said starch is selected from the group consisting of pearl corn starch, corn flour, wheat starch, wheat flour, potato starch, potato flour, mixtures thereof, and mixtures thereof with waxy starch, high amylose starch, or the amylose fraction of a starch.

13. The method of claim 11 wherein the initial solids content of the dispersion is in the range of about 20–40% by weight.

14. The method of claim 11 wherein said starch dispersion is prepared by steam jet cooking.

15. The method of claim 11 wherein the elevated temperature is in the range of about 120°–135° C.

16. The method of claim 11 and further comprising the steps of drying the mixture into a friable mass.

17. The method of claim 11 and further comprising the steps of drying the mixture into a friable mass, particularizing the friable mass into discrete particles, and recovering said particles.

18. The method as described in claim 11 wherein the biologically active chemical is a herbicide, insecticide, fungicide, nematocide, bactericide, rodenticide, molluscicide, acaricide, larvacide, fumigant, animal repellant, plant growth regulator, fertilizer, pheromone, flavor composition, odor composition, vitamin, mineral, or medicament.

19. A method for tailoring the release rate of a biologically active chemical agent encapsulated within a starch matrix, the method comprising:

a. selecting an unmodified starch or mixture of unmodified starches having a ratio of amylose to amylopectin corresponding to a predetermined ratio of amylose and amylopectin needed to impart the desired release properties to said matrix wherein the amylose comprises from about 5% to about 25% of said starch or mixture of starches on a dry weight basis;

b. dispersing said starch or mixture of starches at elevated temperatures in water at an initial solids content of at least about 20% by weight, wherein the granules of starch are completely disrupted and the amylose molecules of the starch are substantially completely disassociated from one another without significant depolymerization;

c. blending said agent into said dispersion to form a mixture of the starch dispersion and the agent, wherein the relative amount of said solids with respect to the agent is sufficient to entrap the agent within a matrix of the starch; and d. dehydrating the mixture consisting essentially of said starch, water and agent under conditions whereby the amylose components will reassociate with one another and thereby transform said mixture at a solids content in the range of about 55–65% into a continuous insolubilized matrix having entrapped therein uniformly dispersed, discontinuous domains of the agent.

20. A method as described in claim 19 wherein the initial solids content of the dispersion is in the range of about 20–40% by weight and said elevated temperature is in the range of about 120°–135° C.

21. A product produced by the method of claims 1, 2, 3, 4, 5, 6, 7, 8, 9, or 10.

22. A product produced by the method of claims 11, 12, 13, 14, 15, 16, 17, 18, 19, or 20.

* * * * *